United States Patent [19]

Albright et al.

[11] 4,083,825
[45] Apr. 11, 1978

[54] NOVEL PHOSPHATE ESTERS AND NON-SCORCHING FLAME RETARDANT POLYURETHANE COMPOSITIONS CONTAINING THEM

[75] Inventors: James A. Albright; Theodore C. Wilkinson, both of Ann Arbor, Mich.

[73] Assignee: Velsicol Chemical Corporation, Chicago, Ill.

[21] Appl. No.: 708,055

[22] Filed: Jul. 23, 1976

[51] Int. Cl.² .......................... C07F 9/09; C08K 5/52
[52] U.S. Cl. .......................... 260/45.7 P; 260/2.5 AJ; 260/963
[58] Field of Search ............ 260/45.7 P, 963, 45.7 RL

[56] References Cited

U.S. PATENT DOCUMENTS

| | | | |
|---|---|---|---|
| 3,132,169 | 5/1964 | Birum et al. | 260/DIG. 24 |
| 3,453,348 | 7/1969 | Demarcq et al. | 260/45.7 P |

*Primary Examiner*—Donald E. Czaja
*Assistant Examiner*—H. H. Fletcher
*Attorney, Agent, or Firm*—Robert M. Phipps

[57] ABSTRACT

Novel triesters of pentavalent phosphorus acid having the formula:

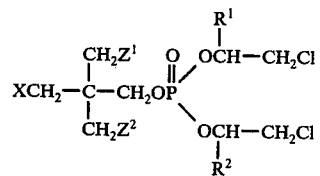

wherein X is chlorine, bromine, or hydrogen, $Z^1$ and $Z^2$ are independently selected from bromine, chlorine, or hydrogen; $R^1$ is methyl, chloromethyl, bromomethyl or hydrogen; and $R^2$ is methyl, chloromethyl or hydrogen, except that $R^2$ is chloromethyl when $R^1$ is bromomethyl, and non-scorching plastic composition containing polyurethanes and said triesters of pentavalent phosphorus acid.

52 Claims, No Drawings

NOVEL PHOSPHATE ESTERS AND NON-SCORCHING FLAME RETARDANT POLYURETHANE COMPOSITIONS CONTAINING THEM

BACKGROUND OF THE INVENYTION

1. Field of the Invention

This invention pertains to plastic compositions containing polyurethane (including, without limitation, rigid foams, semirigid foams, flexible foams, and rubbers). More specifically, the present invention covers plastic compositions containing polyurethanes and certain triesters of pentavalent phosphorus acid as non-scorching flame retardants for said plastic compositions.

2. Description of the Prior Art

Polyurethanes and utility thereof are known in the art as exemplified by Polyurethanes, B.A.B. (Reinhold Plastics Application Series), Reinhold Publishing Corporation, New York, 1965, and *Modern Plastics Encyclopedia* 1972–1973, Vol. 49; No. 10A, October, 1972, pages 110, 112, 162, 276, 278, 279, 282 and 283 and which publications are incorporated herein by reference.

The need for flame retarding polyurethanes has also been recognized in the art as exemplified by U.S. Pat. No. 3,347,822 and *Modern Plastics Encyclopedia*, ibid, pages 222, 456–458 and which publications are in toto incorporated herein by reference.

The use of various prior art materials as flame retardants for polyurethanes has often resulted in certain disadvantages such as thermal migration, head instability, light instability, hydrolytic instability and foam discoloration. Thus, there is always a demand for a material which will function as a flame retardant in polyurethanes and concurrently will not, by incorporation therein, adversely affect the chemical, physical, and mechanical properties and the appearance of the resultant polyuethane composition. This is particularly true with respect to materials which will function as flame retardants in polyurethanes without scorching or discoloring the resultant polyurethanes compositions. For while many of the prior art compounds may function as effective flame retartands in polyurethanes, they may nevertheless adversely affect the color properties of the polyurethanes.

In certain applications and uses of flame retardant poyurethane compositions it is imperative that there be no discoloration thereof. The prior art problem of providing a flame retarded non-scorching polyurethane composition has now been substantially solved by the present invention.

In U.S. Pat. No. 3,132,169, to Birum et al., teaches the use of certain phosphorobromidochloridates and triesters, containing both chlorine and bromine, of pentavalent phosphorus acid as flame retardant agents for polyurethane. However, not all of the compounds taught by the prior art, when incorporated into polyurethane, will result in nonscorching polyurethane compositions. Applicant has discovered a certain narrow and specific class of compounds which, when incorporated into polyurethanes, will provide flame retardancy thereto without discoloration thereof.

SUMMARY OF THE INVENTION

Novel triesters of pentavalent phosphorus acid wherein at least two of said ester groups contain at least one chlorine atom per ester group and novel non-scorching flame retardant plastic compositions containing polyurethanes and said triesters of pentavalent phosphorous acid.

DESCRIPTION OF THE PREFERRED EMBODIMENTS

The novel flame retardant compounds of this invention which will not produce a high degree of scorching or discoloration when incorporated into polyurethane have the general formula:

$$\begin{array}{c} \phantom{XCH_2-}\overset{CH_2Z^1}{\underset{CH_2Z^2}{|}}\phantom{-} \\ XCH_2-C-CH_2OP \\ \end{array} \overset{O}{\underset{\phantom{O}}{\|}} \begin{array}{c} \overset{R^1}{|} \\ OCH-CH_2Cl \\ OCH-CH_2Cl \\ \underset{R^2}{|} \end{array} \quad (I)$$

wherein X is chlorine, bromine or hydrogen; $Z_1$ and $Z_2$ are independently selected from bromine, chorine or hydrogen; $R_1$ is methyl, bromomethyl, chloromethyl or hydrogen; and $R_2$ is methyl, chloromethyl or hydrogen, except that $R_2$ is chloromethyl when $R_1$ is bromomethyl.

Illustrative (but without limitation) of some of the present invention phosphate compounds falling within formula I above are set forth below with the exemplary definitions of X, $Z_1$, $Z_2$, $R_1$ and $R_2$ listed in Table I.

TABLE I

| Compound No. | X | $Z_1$ | $Z_2$ | $R_1$ | $R_2$ |
|---|---|---|---|---|---|
| 1 | Cl | Br | Br | H | H |
| 2 | Cl | H | H | —CH$_2$Cl | —CH$_2$Cl |
| 3 | Cl | Cl | Cl | —CH$_3$ | —CH$_3$ |
| 4 | Cl | Br | Br | —CH$_2$Cl | —CH$_2$Cl |
| 5 | Br | Br | Br | —CH$_2$Cl | —CH$_2$Cl |
| 6 | Br | H | H | —CH$_2$Br | —CH$_2$Cl |

In general, these compounds can be prepared in known manner, by:

1. reaction of phosphoryl chloride with a neopentyl alcohol of the general formula:

$$XCH_2-\underset{\underset{CH_2Z_2}{|}}{\overset{\overset{CH_2Z_1}{|}}{C}}-CH_2OH$$

wherein X, $Z_1$, and $Z_2$ are as aforedefined, to form a dichlorophosphate of the formula:

$$XH_2C-\underset{\underset{CH_2Z_2}{|}}{\overset{\overset{CH_2Z_1}{|}}{C}}-CH_2O\overset{O}{\underset{\phantom{O}}{\overset{\|}{P}}}\begin{array}{c} Cl \\ Cl \end{array} \quad ; \text{and} \quad (II)$$

2. reaction of the dichlorophosphate of formula II with epoxide having the formula:

$$\underset{CH_2-CH-R_1}{\overset{O}{\diagdown\diagup}} \quad \text{and/or} \quad \underset{CH_2-CH-R_2,}{\overset{O}{\diagdown\diagup}}$$

wherein $R_1$ and $R_2$ are defined above, to form the phosphate of formula I.

An alternate method for preparing certain of the compounds of formula I, i.e., those compounds of formula VII below, comprises: (1) reacting a glycol of the formula:

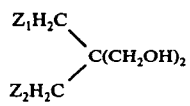

with phosphorus trichloride to form compounds of the formula:

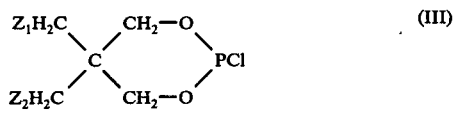

wherein $Z_1$ and $Z_2$ are as defined above;

2. reacting compounds of formula III with $Cl_2$ or $Br_2$ to cleave the cyclic structure of formula III and produce a compound having the formula:

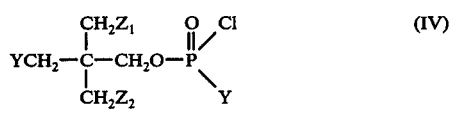

wherein $Z_1$ and $Z_2$ are as defined above and Y is chlorine or bromine; and 3. reacting compound IV with appropriate epoxides of the formula

and

to form some of the compounds of the present invention, i.e., those having the formula:

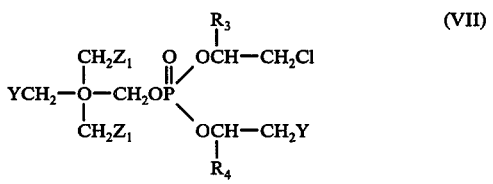

wherein $Z_1$ and $Z_2$ are as defined above; Y is bromine or chloride; $R_3$ is methyl, chloromethyl, methyl, or hydrogen; and $R_4$ is methyl, chloromethyl, or hydrogen, except that (i) if Y is bromine, then both $R_3$ and $R_4$ are chloromethyl, and (ii) if $R_3$ is bromomethyl then $R_4$ is chloromethyl, The above reactions generally proceed quite readily and usually no special reaction conditions or chemical processing equipment need be employed. These reactions can be conducted at room temperatures, temperatures above ambient, and temperatures below ambient. Elevated temperatures may be used to insure completion of the reaction, although some of the foregoing addition reactions are generally exothermic and it may be advisable, at least initially, to use external cooling. It is generally preferable, although not essential, to employ solvents such as halogenated hydrocarbons like methylene chloride and chlorobenzene. The amount of reactants used in the above reactants is preferably stoichiometric, although an excess of either reactant can be used. While the presence of a catalyst is generally not mandatory one may be used to decrease reaction times and allow the use of lower reaction temperatures.

In another embodiment of the present invention there are provided novel substantially non-scorching plastic compositions containing polyurethane and having incorporated therein an effective amount of the flame retardant compound of formula I. By the term effective amount is meant an amount of compound of formula I which is effective to impart flame retardancy to the composition. That is, the amount of the phosphate compound of formula I employed in the present invention compositions is any quantity which will effectively render the polyurethane composition flame retardant or effectively reduce the combustibility of said composition without at the same time unduly discoloring or scorching said composition. Generally, the amount used is from about 1 to 50 percent by weight, based on the total weight of the composition. Preferably, the amount employed is from about 2 to 30 percent, more preferably from 5 to 25 percent, and most preferably from about 5 to 20 percent. It is to be understood that generally any amount may be used so long as this amount does not substantially adversely affect the chemical, physical, and mechanical properties, and/or appearance of the end polyurethane composition.

It is to be understood that the term polyurethanes as used herein means polymers containing repeated urethane linkages:

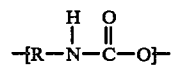

when R is aromatic or aliphatic group. These polymers are generally made by reacting a polyisocyanate with a compound having a plurality of hydroxyl groups.

Thus the polyurethanes used in the present invention compositions is any polyurethane herein defined and which one so desires to flame retard. It is to be understood that the polyurethanes used can be a "virgin" material, i.e., substantially free of additives such as stabilizers, plasticizers, dyes, pigments, fillers, and the like, or the polyurethanes can have additives (such as those mentioned and described herein) already contained therein or added concurrently with or after the addition of the phosphate compounds of formula I. These polyurethane compositions include: rigid foams, semi-rigid foams, flexible foams, rubbers and adhesives.

It is also within the scope of the present invention to employ other materials in the present invention compositions where one so desires to achieve a particular end result. Such materials include, without limitation, adhesion promotors; antioxidants; antistatic agents; antimicrobials; colorants; flame retardants such as those listed on pages 456–458, Modern Plastics Encyclopedia, ibid. (in addition to the new class of flame retardants described herein); heat stabilizers; light stabilizers; pigments; plasticizers; preservatives; ultraviolet stabilizers and fillers.

In this latter category, i.e., fillers, there can be mentioned, witout limitation, materials such as glass; carbon; cellulosic fillers (wood flour, cork and shell flour); calcium carbonate (chalk, limestone, and precipitated calcium carbonate); metal flakes; metallic oxides (aluminum, beryllium oxide and magnesia); metallic powders (aluminum, bronze, lead, stainless steel and zinc); polymers (comminuted polymers and elastomer-plastic blends); silica products (diatomaceous earth, novaculite, quartz, sand, tripoli, fumed colloidal silica, silica aerogel, wet process silica); silicates (asbestes, kaolimite, mica, nepheline syenite, talc, vollastonite, such as barium ferrite, barium sulfate, molybdenum disulfide and silicon carbide. The above mentioned materials, including fillers, are more fully described in Modern Plastics Encyclopedia, ibid., and which publication is incorporated herein by reference.

The amount of the above described materials employed in the present invention compositions can be any quantity which will not substantially adversely affect the desired results derived from the present invention compositions. Thus, the amount used can be zero percent, based on the total weight of the composition, up to that percent at which the composition can still be classified as a plastic. In general, such amount will be from about 0 to about 75 percent and specifically from about 1 to about 50 percent.

The following examples are provided for the purpose of further illustration only and are not intended to be limitations on the disclosed invention. Unless otherwise specified, all temperatures are expressed in degrees centigrade; all weights are expressed in grams; and all volumes are expressed in milliliters.

EXAMPLE 1

To a suspension containing 200 ml of methylene chloride and 145.6 gms of neopentyl glycol was added, dropwise, 192.4 gms of phosphorus trichloride while the reaction mixture was maintained at 10° C. After addition of the phosphorus trichloride was completed the reaction mixture was heated to 35° C. and maintained at this temperature for one half hour. Methylene chloride was then removed from the reaction mixture under vacuum. The temperature of the reaction mixture was then lowered to below 20° C. and chlorine gas was introduced until the reaction mixture was yellow in color. The excess chlorine was then removed and a titanium tetrachloride catalyst was introduced. The reaction mixture was then heated to 80° C. and 259 gms of epichlorohydrin was added dropwise. The reaction mixture was maintained at 80° C. for 1 hour after addition of epichlorohydrin was complete. The resulting product was washed with aqueous ammonia followed by two washings with deionized water. The product was dried under vacuum and filtered hot to yield 542 gms of a clear liquid which was substantially bis(dichloropropyl)-2,2-dimethyl-3-chloropropyl phosphate (compound 2 in Table I).

EXAMPLE 2

To a suspension containing 62.4 gms of neopentyl glycol in 200 ml of methylene chloride was added 82.5 gms of phosphorus trichloride. The reaction mixture was kept below 10° C. during the addition of the phosphorus trichloride. The reaction mixture was then heated to 40° C. and kept at this temperature for one half hour. The mixture was then brought to below 20° C. and 96 gms of bromine was dded while cooling the mixture to keep the temperature below 20° C. The methylene chloride solvent was then removed under vacuum and 0.8 gms of titanium chloride catalyst was introduced and the mixture was heated to 60° C. One hundred eleven gms of epichlorohydrin was added to the mixture. This resulted in an exothermic reaction which raised the temperature to between 80° and 90° C. The reaction mixture was held at 80° C. for one half hour after the addition of the epichlorohydrin. The reaction mixture was then cooled and the product was washed with aqueous ammonia followed by two washings with deionized water. Thereafter the material was dried and filtered. The resultant yellow liquid weighed 286 gms and was substantially 3-bromo-2,2-diethylpropyl-1-bromo-3-chloro-2-propyl-1,3-dichloro-2-propyl phosphate (compound 6 in Table I).

EXAMPLE 3

To a solution of 153.5 gms of phosphoryl chloride and 2.0 gms of titanium tetrachloride, heated to 50° C., was added 325 gms of tribromoneopentyl alcohol. The resulting reaction mixture was heated for 4 hours at 80° C. One hundred eighty-five gms of epichlorohydrin was added to the reaction mixture and the resulting reaction system was kept at 90° C. for 2 hours. At the end of this period the product was washed with deionized water, followed by an aqueous ammonia wash, and again washed with deionized water. The washing was followed by drying and filtering. The end product was 430 gms of substantially bis-(1,3-dichloro-2-propyl) tribromoneopentyl phosphate (compound 5 of Table I).

EXAMPLE 4

One hundred seventy-three gms of dichloroneopentyl glycol was added, at room temperature, to 137 gms of phosphorus trichloride. The resultant reaction mixture was heated to 90° C. and maintained thereat for 4 hours. The mixture was then cooled and 150 ml of metylene cloride was added thereto. The resulting solution was kept below 20° C. and chlorine gas was added below the suface of the liquid. The methylene chloride was then removed under vacuum. Titanium tetrachloride (0.1 gms) was introduced into the reaction mixture and the mixture was heated to 80° C. for 4 hours. The resulting product was washed with deionized water, aqueous ammonia, and thereafter dried and filtered. The product was substantially bis-(1-chloro-2-propyl) trichloroneopentyl phosphate (compound 3 in Table I), a medium viscosity liquid weighing 226 gms.

EXAMPLE 5

To 371.3 gms of phosphorus trichloride, maintained at 0° C., was slowly added 707.4 gms of dibromoneopentyl glycol. The mixture was then heated for 3 hours at 70° C. On cooling 500 ml of methylene chloride was added and chlorine gas bubbled through the resultant solution. Titanium tetrachloride (0.2 gms) was then added and the mixture was heated to 80° C., at which time 499.5 gms of epichlorohydrin was added. After the addition of the epichlorohydrin the reaction mixture was kept at 90° C., by the application of external heat, for three hours. On cooling the resultant product was washed with deionized water, followed by an aqueous ammonia wash. This was followed by two further washings with deionized water. The product was then dried and filtred. The recovered product was substantially bis-(1,3-dichloro-2-propyl)-3-chloro-2,2-dibromomethyl-1-propyl phosphate (compound 4 of Table I).

EXAMPLE 6

Four hundred twelve gms of phosphorus trichloride was cooled in ice to 10° C. and 786 gms of dibromoneopentyl glycol was added thereto. An endothermic reaction developed with the evolution of hydrogen chloride. After 2 hours the ice bath was removed and the product was heated to 50° C. for 1 hour, then aspirated for 1 hour at this temperature. The product was then cooled and 500 ml of methylene chloride was added. One hundred ninety-seven gms of chlorine was then added, keeping the resultant exothermic reaction below 30° C. Upon complete addition of chlorine, the methylene chloride was removed under vacuum and a viscous clear liquid resulted. This intermediate was then used in Example 7 to form bis-(2-chloroethyl)-2,2-bis-bromomethyl-3-chloropropyl phosphate.

EXAMPLE 7

To 397 gms of the viscous clear liquid of Example 6 was added 3 gms of titanium tetrachloride. This mixture was heated to 65° C. and 88 gms of ethylene oxide was added. The resulting reaction was exothermic and the addition took 2 hours. The reaction mixture was aspirated for one half hour at 60° C. and washed with water followed by washing with aqueous ammonia and two further water washes. Celite ® brand of diatomaceous earth filter aid Celkate ® brand of magnesium silicate filter aid were added and the product was dried under vacuum. After filtering 428 gms of a colorless liquid resulted. This liquid was substantially bis-(2-chloroethyl)-2,2-bis-bromomethyl-3-chloropropyl phosphate (compound 1 of Table I).

The novel compounds of formula I can be incorporated with the polyurethanes at any processing stage in order to prepare the novel compositions. In general this is undertaken prior to fabrication either by physical blending or during the process of forming polyurethanes per se.

EXAMPLE 8

Separate flexible polyurethane foam compositions (designated 1–9 in Table II) were prepared via the following procedure: formulation No. 1 was the control and did not contain a phosphate compound.

Approximately 500 gms polyol (Dow Chemical Co.'s Voranol 3010— a glycerine based propylene oxide polyol of about 3,000 mol. wt. and a hydroxyl number of about 46 to 47), 5.0 gm surfactant (Union Carbide Corp.'s L 5720—a silicone based material) 35.0 gms Freon ® brand of fluorocarbon blowing agent and 45 gms of each flame retardant compound indicated in Table II were mixed together. 293.0 gms of toluene diisocyanate was added to the polyol mix and allowed to settle to the bottom. 2.25 gms of amine catalyst (Union Carbide Corp.'s Niax A-1) was mixed with 15.0 gms of water and the resultant mixture was added to the polyol mix and allowed to float on a portion of the surface thereof. 1.5 gms of stannous octoate was added to the polyol mix and the mixture was stirred for 6 seconds at 1300 rpm. The mixture was quickly discharged into a gallon paper container. The foam was then allowed to rise. After the foam had completely risen, it was allowed to set and was then post cured at 121° F. for 30 minutes.

Portions of the samples of each perspective formulation (Nos. 1–9, Table II) prepared according to the above described procedure were then subjected to a standard flammability test and to a color determination test. The results of these tests are shown in Table II.

TABLE II

Scorch and Flammability of Flexible Urethane Foams as Measured by the Gardner Colorimeter and the California Vertical Burn Test

| Formulation No. | Compound | L | $a_L$ | $b_L$ | $\Delta E$ | Maximum Char Length | | | Average Char Length | | |
|---|---|---|---|---|---|---|---|---|---|---|---|
| | | | | | | Initial | Aged 2 wks 150° F. | Aged 2 wks 250° F. | Initial | Aged 2 wks 150° F. | Aged 2 wks 250° F. |
| 1 Invention | Control | 75.2 | −0.5 | +0.3 | — | 12.0 | 12.0 | 12.0 | 12.0 | 12.0 | 12.0 |
| 2 | Example No. 7 | 72.3 | −1.3 | +2.1 | 3.5 | 5.8 | 5.4 | 4.5 | 5.0 | 5.4 | 3.6 |
| 3 | Example No. 1 | 69.1 | −0.7 | +0.4 | 6.1 | 8.0 | 6.9 | 8.1 | 6.8 | 6.4 | 7.1 |
| 4 | Example No. 3 | 71.2 | −0.3 | −0.5 | 4.2 | 6.4 | 5.9 | 5.5 | 5.7 | 5.3 | 5.0 |
| 5 | Example No. 4 | 71.1 | −0.3 | +0.0 | 4.1 | 7.8 | 8.9 | 8.4 | 6.6 | 7.7 | 6.9 |
| 6 Comparative | Example No. 2 | 71.1 | −1.0 | +2.8 | 4.9 | 5.7 | 5.8 | 4.3 | 5.3 | 5.0 | 3.7 |
| 7 | Bis-(bromopropyl) chloroethyl phosphate | 64.4 | −0.5 | +0.3 | 10.9 | 5.4 | 5.9 | — | 4.7 | 5.4 | — |
| 8 | 3-bromo-2,2-dimethyl-propyl-1-bromo-2-propyl-1-chloro-2-propyl phosphate | 63.3 | −0.5 | +0.5 | 11.9 | 6.5 | 6.7 | 5.0 | 5.5 | 5.8 | 4.4 |
| 9 | Tris-(chloropropyl) phosphate | 69.9 | −0.3 | −0.4 | 5.4 | 6.8 | 7.2 | 12.0 | 6.2 | 6.6 | 12.0 |

The California Vertical Burn Test utilized in Table II above is fully set forth in State of California, Department of Consumer Affairs, Bureau of Home Furnishings, Technical Information Bulletin 117. This test is, in general, the application of a flame to a test specimen (strip) for 12 seconds and the timing of the burning for a specified length of the strip. In this test to be acceptable the average afterflame, including afterflame of molten material dropping from the specimen, shall not exceed 5 seconds; the average afterglow, including afterglow of molten material dropping from the specimen, shall not exceed 15 seconds; the average char length shall not exceed 6 inches; the maximum char length of any individual specimen shall not exceed 8 inches; foam products shall meet the above requirements both before and after aging for 14 days in a forced air circulating oven at 150° F.

In the Gardner Colorimeter Test reported in Table II above for the discoloration determination a Gardner XL10-CDM colorimeter was used to measure the color development. Cross-sectional pieces were used from the foams. Five samples were cut and both sides measured and averaged. The terminology is defined as $\Delta E$ a color difference representative of human eye response derived from the formula:

$$\Delta E = [(L_2 - L_1)^2 + (a_{L2} - a_{L1})^2 + (b_{L2} - b_{L1})]^{\frac{1}{2}}$$

where L, $a_L$, and $b_L$ are measured values.

The significance of light stability of plastic compositions is recognized in the art, e.g., the publication entitled "The Measurement Of Appearance" by Mr. Richard S. Hunter (Hunter Assocaites Laboratory, Inc., 9529 Lee Highway, Fairfax, Va. 1973. Mr. Hunter has been associated with the efforts of defining appearance and color since the 1930's and was for many years an associate of Gardner who is another authority in this field. The following paragraphs from Mr. Hunter's book are set forth in order to demonstrate this light stbility significance.

The Judd-Hunter system "of scales for color difference was based on Judd's uniform chromaticity scales triangle. Judd made an instrumental study of a number of woolen swatches rated by dyers for their acceptability as commercial color matches to standard. The NBS unit of color difference was designed by Judd to be the maximum difference commercially acceptable in the textile trade as represented by these dyers at the time when the study was carried out (Judd, 1939). The NBS Unit generally referred to today is not Judd's 1939 unit, but the Hunter 1942 version of the Judd unit with 100 units falling between black and white."

"Since 1942 this unit has been used in terms of a number of the opponent color scales. In a color scale which is already uniform in its visual spacing of lightness and chromaticity, and which has 100 units between black and white as well as rectangular coordinates for chromaticity, color difference in approximate NBS units can be specified in units of that system. The color difference becomes the distance between the two colors in that color space. With rectangular coordinates, the formula is:

$$\Delta E = \sqrt{\Delta L^2 + \Delta a^2 + \Delta b^2}$$

Similarly if only the chromaticity component of difference is desired, the formula is:

$$\Delta C = \sqrt{\Delta a^2 + \Delta b^2}$$

"Following Judd's proposed unit of color differene, Hunter proposed the measurement of much the same quantity by a photoelectric tristimulus method in 1942. In the next year, Scofield proposed a quantity which was quite a bit easier to compute. Scofield used the reciprocal of the square root of reflectance instead of the reciprocal of the fourth root of reflectance as a multiplier in adjusting reflecting values for uniform lightness scale intervals. This is the only difference between the Scofield and the Judd-Hunter formulas for color difference. (Scofield, 1943)."

"In 1948, Hunter started to develop a tristimulus instrument which would read chromaticity dimensions of opponent colors directly. He was seeking to improve the precision and usefullness of results of the tristimulus reflectometers previously used. The $R_d$ scales developed in the period 1948 and 1950 did not have a uniform lightness readout but did have direct reading visually uniform a and b scales. The L scales, in which there is approximate perceptual uniformity in all three dimensions, were created in the period 1950-1952 but were not described in a formal publication until 1958. These two sets of Hunter Color Difference Meter scales enjoy wide use because of the fact that they can be read directly from a tristimulus instrument with high precision, and offer instrumental computation of color difference by the $\Delta E$ formula given above."

"NBS Unit of Color Difference is defined as: the unit of color difference of the National Bureau of Standards. The unit is above four times as great as the smallest difference observable under ideal conditions. Differences of less than one unit are usually not important in commercial transactions. In Munsell terms, one NBS unit is equivalent to about 0.1 Valve step, 0.15 Chroma step, or 2.5 Hue step at Chroma 1."

"Hunter further investigated the use of $L'$, $\alpha'$, $\beta'$ for color difference measurement. He recognized at this time (which no other color-difference scale before or since has recognized that perceived color difference will depend on the proximity of the speciment compared and on their glossiness. Accordingly, the 1942 Hunter color difference equation includes factors to account for these variables. It is this equation, with selected constants, that defines the widely used NBS unit of color difference."

"High precision is almost always essential for useful color difference measurements. Only with precise instruments is it possible to measure color difference as small as those the eye can see. Instrument accuracy is also normally a requisite because spectrally inaccurate instruments, even though precise, will give visually inaccurate color difference measurements wherever there are spectral differences between the specimens involved. The ease of obtaining and interpreting values of color difference is another factor which may affect the selection of a procedure."

"Twenty years ago, color difference scales were in demand to serve as a basis for setting one-number tolerances for fading and acceptability of matches. The Index of Fading and NBS unit were used as units."

"Today, the concept of color difference is more refined. One number tolerances are seldom used. Instead, color difference tolerances are designed as boundaries in color space within which acceptable colors must fall. The boundaries do not necessarily correlate with perceptibility of difference but rather with the limits of acceptability. The standard color, furthermoe, may not be in the center of the bounded region but may be displaced to one side. For example, where subsequent yellowing may occur, the tolerance for the yellow-blue dimension might be +0.1, −0.8 units."

"Color difference specifications are tighter today and tolerances are smaller. The specification usually treats the color dimensions separately so that a complete specification would contain nine numbers: The three numbers that describe the desired color, and the six numbers that describe the individual plus and minus tolerances. Such tolerances can be reduced to graphs which not only show acceptability but provide a guide to the formulation correction needed to correct an of shade. When the question of acceptability becomes a question of sorting objects according to shade, a graphical chart showing the classification of color values can be quite helpful."

"Although color measurements are frequently used for identification, sorting and recording of color values, the primary uses of tristimulus instruments all involve measurements of fairly small color differences. The most frequent uses of these small color differences measurements are to establish closeness to standard and to give guidance for the adjustment of color mismatches. They are also used in the study of deterioration in a produce as a result of exposure and use."

"Spectrophotometers and tristimulus instruments made up the majority of color appearance measuring instruments in use in industry. Spectrophotometers give wavelength-by-wavelength analyses of the reflecting properties of objects, while tristimulus instruments by the use of filters which approximate the Standard Observer functions of the eye, give measurements of color in X, Y, Z terms, or in L, a, b values. Spectrophotometers are essential where color formulation is involved, and metamerism must be controlled. However, tristimulus colorimeters and reflectometers provide precise and less expensie means for the routine measurement of color and adjudgement of small color differenes."

In view of the foregoing quoted subject matter, it can thus be seen that a change in Δ E value of 1 unit constitutes a real change. It is to be noted that a lower ΔE value is more desired and the higher Δ E value is least desired. This Δ E value is not an abstract value, however, since one must compare it with the Δ E values of the "control" plastic composition. One of the desired Δ E values would be where both the Δ E values of the "control" plastic composition (without additives—i.e., without flame retardant and enhancing agent) and the plastic composition with said additives are substantially the same or the latter has a lower value.

As is evident from Table II the polyurethane compositions of the present invention, i.e., formulations 2–6 in Table II, are both flame retardant and non-discolored, i.e., have relatively low Δ E values. (The higher the Δ E value the greater the discoloration.) The control formulation 1 in Table II, while not discolored, was not flame retardant. The tris(choloropropyl)phosphate containing polyurethane composition (formulation 9 in Table II), while having a relatively low discoloration, i.e., Δ E value of 5.4, was not fire-retardant after aging for 2 weeks at 250° F. and gave the same results on the Burn Test as the control. The bis-(bromopropyl) chloroethyl phosphate (formulation 7 in Table II) and 3-bromo-2,2-dimethylpropyl-1-bromo-2-propyl-1-chloro-2-propyl phosphate (formulation 8 in Table II) polyurethane compositions, while being flame retardant, were relatively highly discolored, i.e., had relatively high Δ E values of 10.9 and 11.9, respectively. Thus all three of these polyurethane compositions (Nos.7–9 in Table II) failed to meet the criteria necessary for flame retardant non-scorching polyurethane compositions.

Compositions 7-9 above contain compounds which are representative of compounds outside the invention as claimed herein. Compositions 7 and 8 contain compounds which fall within the scope of Birum et al.

The superior non-scorching and flame retardant nature of the polyurethane compositions within the scope of the present invention as claimed has significant commercial implications. These superior properties of flame retarding and color stability of the present compositions, which utilize the aforedescribed compounds falling within the narrow group as defined by formula I, are not possessed by the structurally relatively close prior art compounds. The term scorch, as used herein, includes discoloration and/or loss of physical properties of the polyurethane composition. This phenomenon is generally observed in the center of the polyurethane composition. Although not thoroughly understood scorch is believed to be caused by thermal instability, hydrolytic instability, or the reaction of the flame retardant compound with other components of the polyurethane composition. Generally, polyurethane manufacturers are reluctant to incorporate flame retardants which result in scorch because of the adverse appearance and physical properties of the end polyurethane composition.

In view of the foregoing Examples an remarks, it is seen that the plastic compositions, which incorporate the compounds of formula I, possess characteristics which have been unobtainable in the prior art. Thus, the use of these compounds in the above described plasti polyurethane material as flame retardants therefore is quite unique since it is generally not possible to predict the effectiveness and functionality of any particular material in any polymer system until it has actively undergone incorporation therein and the resultant composition has been subjected to testing. For as seen in the date in Table II, compounds which are structurally similar to compounds of formula I nevertheless give results when incorporated into polyurethane compositions, quite different from those achieved by using compounds of formula I. Furthermore, it is necessary, in order to have commercial utility, that the resultant flame retarded plastic polyurethane compostion be non-scorched or non-discolored. Use of these compounds in the polyurethane materials has accomplished all of these objectives.

The above examples have been described in the foregoing specification for the purpose of illustration and not limitation. Many other modifications and ramifications will naturally suggest themselves to those skilled in the art based on this disclosure. These are intended to be comprehended as within the scope of this invention.

The embodiments of the invention in which an exclusive property or privilege is claimed are defined as follows:

1. A substantially non-scorching plastic composition containing polyurethane having incorporated therein an effective amount of a flame retardant compound having the formula:

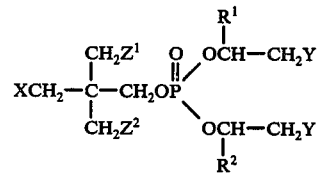

wherein X is chlorine, bromine or hydrogen; Z¹ is chlorine, bromine or hydrogen; Z² is chlorine, bromine or hydrogen; Y is chlorine; R¹ is methyl, chloromethyl, bromomethyl or hydrogen; and R² is methyl, chloromethyl or hydrogen, except that R² is chloromethyl when R¹ is bromomethyl.

2. The composition as set forth in claim 1 wherein R¹ is chloromethyl.

3. The composition as set forth in claim 2 wherein R² is chloromethyl.

4. The composition as set forth in claim 3 wherein Z¹ is bromine.

5. The composition as set forth in claim 4 wherein Z² is bromine.

6. The composition as set forth in claim 5 wherein X is chlorine.

7. The composition as set forth in claim 5 wheein X is bromine.

8. The composition as set forth in claim 3 wherein Z¹ is hydrogen.

9. The composition as set fotrh in claim 8 wherein Z² is hydrogen.

10. The composition as set forth in claim 9 wherein X is chlorine.
11. The composition as set forth in claim 1 wherein $R^1$ is hydrogen.
12. The composition as set forth in claim 11 wherein $R^2$ is hydrogen.
13. The composition as set forth in claim 12 wherein $Z^1$ is bromine.
14. The composition as set forth in claim 13 wherein $Z^2$ is bromine.
15. The composition as set forth in claim 14 wherein X is chlorine.
16. The composition as set forth in claim 1 wherein $R^1$ is methyl.
17. The composition as set forth in claim 16 wherein $R^2$ is methyl.
18. The composition as set forth in claim 17 wherein $Z^1$ is chlorine.
19. The composition as set forth in claim 18 wherein $Z^2$ is chlorine.
20. The composition as set forth in claim 18 wherein X is chlorine.
21. The composition as set forth in claim 1 wherein $R^1$ is bromomethyl and $R^2$ is chloromethyl.
22. The composition as set forth in claim 21 wherein $Z^1$ is hydrogen.
23. The composition as set forth in claim 22 wherein $Z^2$ is hydrogen.
24. The composition as set forth in claim 23 wherein X is bromine.
25. The composition as set forth in claim 1 wherein $R^1$ is bromomethyl and $R^2$ is chloromethyl, $Z^1$ and $Z^2$ are hydrogen, and X is bromine.
26. The composition as set forth in claim 1 wherein $R^1$ and $R^2$ are chloromethyl, and $Z^1$, $Z^2$ and X are bromine.
27. A compound of the formula:

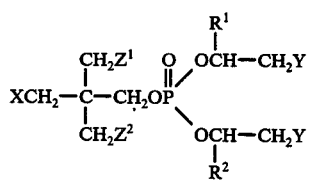

wherein X is chlorine, bromine or hydrogen; $Z^1$ is chlorine, bromine or hydrogen; $Z^2$ is chlorine, bromine or hydrogen; Y is chlorine; $R^1$ is methyl, chloromethyl, bromomethyl or hydrogen; and $R^2$ is methyl, chloromethyl or hydrogen, except that $R^2$ is chloromethyl when $R^1$ is bromomethyl.

28. The compound as set forth in claim 27 wherein $R^2$ is chloromethyl.
29. The compound as set forth in claim 28 wherein $R^2$ is chloromethyl.
30. The compound as set forth in claim 29 wherein $Z^1$ is bromine.
31. The compound as set forth in claim 30 wherein $Z^2$ is bromine.
32. The compound as set forth in claim 31 wherein X is chlorine.
33. The compound as set forth in claim 31 wherein X is bromine.
34. The compound as set forth in claim 29 wherein $Z^1$ is hydrogen.
35. The compound as set forth in claim 34 wherein $Z^2$ is hydrogen.
36. The compound as set forth in claim 35 wherein X is chlorine.
37. The compound as set forth in claim 27 wherein $R^1$ is hydrogen.
38. The compound as set forth in claim 37 wherein $R^2$ is hydrogen.
39. The compound as set forth in claim 38 wherein $Z^1$ is bromine.
40. The compound as set forth in claim 38 wherein $Z^2$ is bromine.
41. The compound as set forth in claim 39 wherein X is chlorine.
42. The compound as set forth in claim 27 wherein $R^1$ is methyl.
43. The compound as set forth in claim 42 wherein $R^2$ is methyl.
44. The compound as set forth in claim 43 wherein $Z^1$ is chlorine.
45. The compound as set forth in claim 44 wherein $Z^2$ is chlorine.
46. The compound as set forth in claim 45 wherein X is chlorine.
47. The compound as set forth in claim 27 wherein $R^1$ is bromomethyl and $R^2$ is chloromethyl.
48. The compound as set forth in claim 47 wherein $Z^1$ is hydrogen.
49. The compound as set forth in claim 48 wherein $Z^2$ is hydrogen.
50. The compound as set forth in claim 49 wherein X is bromine.
51. The compound as set forth in claim 27 wherein $R^1$ is bromomethyl and $R^2$ is chloromethyl, $Z^1$ and $Z^2$ are hydrogen, and X is bromine.
52. The compound as set forth in claim 27 wherein $R^1$ and $R^2$ are chloromethyl, and $Z^1$, $Z^2$ and X are bromine.

* * * * *

UNITED STATES PATENT OFFICE
CERTIFICATE OF CORRECTION

PATENT NO. : 4,083,825
DATED : April 11, 1978
INVENTOR(S) : J. A. Albright et al.

It is certified that error appears in the above-identified patent and that said Letters Patent are hereby corrected as shown below:

Column 1, line 8 after the word of delete: INVENYTION and insert: -- INVENTION --.

Column 14, line 2 (the same being claim 28, line 2)

delete: $R^2$ and insert -- $R^1$ --.

Signed and Sealed this

Twenty-eighth Day of November 1978

[SEAL]

Attest:

RUTH C. MASON
Attesting Officer

DONALD W. BANNER
Commissioner of Patents and Trademarks